United States Patent [19]

Nishi

[11] Patent Number: 4,671,790
[45] Date of Patent: Jun. 9, 1987

[54] APPARATUS FOR ASPIRATING LENS CORTEX WITH VACUUM CREATING DEVICE

[75] Inventor: Okihiro Nishi, Katano, Japan

[73] Assignee: Gyokusen Kosan Kabushiki Kaisha, Osaka, Japan

[21] Appl. No.: 816,525

[22] Filed: Jan. 6, 1986

[30] Foreign Application Priority Data

Mar. 4, 1985 [JP] Japan ............................ 60-30608[U]

[51] Int. Cl.⁴ ............................................ A61M 37/00
[52] U.S. Cl. .................................... 604/131; 604/147
[58] Field of Search ............... 604/22, 27, 32–35, 604/48, 119–121, 131, 147, 902; 417/211, 470

[56] References Cited

U.S. PATENT DOCUMENTS

| | | | |
|---|---|---|---|
| 1,583,487 | 5/1926 | Parkler | 604/34 |
| 2,142,624 | 1/1939 | Williams | 604/131 |
| 4,024,866 | 5/1977 | Wallach | 604/22 |
| 4,519,385 | 5/1985 | Atkinson et al. | 604/27 |

FOREIGN PATENT DOCUMENTS 2117245 10/1983 United Kingdom ............... 604/902

Primary Examiner—C. Fred Rosenbaum
Assistant Examiner—J. L. Kruter
Attorney, Agent, or Firm—Armstrong, Nikaido, Marmelstein & Kubovcik

[57] ABSTRACT

An apparatus for aspirating the lens cortex which comprises an aspirator and a negative pressure generator. The aspirator comprises a handpiece having an aspirating nozzle and an irrigating nozzle adjacent to the nozzle, an aspirating tube being connected to the aspirating nozzle to provide an aspirating channel extending from the aspirating nozzle through the tube, the aspirating channel having a shutoff member for opening or closing the channel. The negative pressure generator comprises a barrel attached to a mount frame and fitted with a plunger, the barrel having an open connecting end for holding the barrel in communication with the aspirating nozzle, the plunger having a weight engaging portion.

2 Claims, 7 Drawing Figures

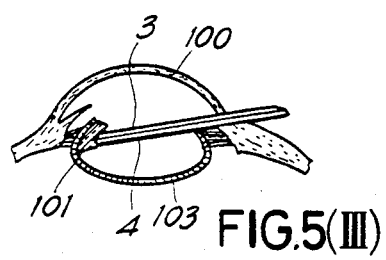
FIG.5(III)

4,671,790

APPARATUS FOR ASPIRATING LENS CORTEX WITH VACUUM CREATING DEVICE

TECHNICAL FIELD

The present invention relates to an apparatus for use in extracapsular cataract extraction for aspirating the lens cortex.

PRIOR ART AND PROBLEMS

An aspirator comprising an aspirator nozzle connected to an electrically driven vacuum pump is usually used for removing the lens cortex.

However, the aspirator is expensive and inconvenient to transport because the electric vacuum pump is a large-sized precision device. Moreover, the aspirator is not usable in uncivilized areas, secluded places or the like where it is difficult to obtain a power supply.

Although the operation can be performed utilizing the suction of a syringe, the surgeon must handle the syringe with both hands and encounters difficulty.

The plunger of the syringe can be withdrawn by an assistant, but the suction then is not controllable as desired by the surgeon.

SUMMARY OF THE INVENTION

An object of the present invention is to provide an apparatus for use in extracapsular cataract extraction which is capable of removing the lens cortex by aspiration without using any power supply equipment.

Another object of the present invention is to provide an apparatus for aspirating the lens cortex which comprises an aspirator and a negative pressure generator.

The aspirator of the present invention comprises a handpiece supportable by one hand and provided with an aspirating nozzle and an irrigating nozzle adjacent to the nozzle, an aspirating tube being connected to the aspirating nozzle to provide an aspirating channel extending from the nozzle through the tube, the aspirating channel having a shutoff member for opening or closing the channel.

The negative pressure generator of the present invention comprises a barrel attached to a mount frame and fitted with a plunger, the barrel having an open connecting end for holding the barrel in communication with the aspirating nozzle, the plunger being provided with a weight engaging portion.

DETAILED DESCRIPTION OF THE INVENTION

The above and other objects of the present invention will become more apparent from the following detailed description with reference to the accompanying drawings.

Figure 1:
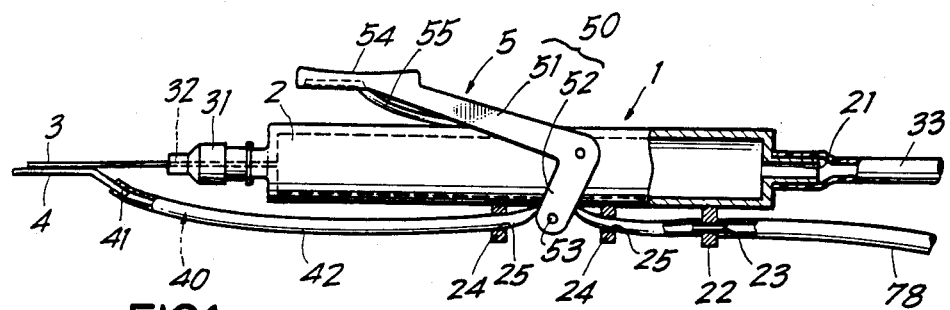
FIG. 1 is a front view partly broken away and showing an aspirator of the present invention.

With reference to FIG. 1 showing an aspirator 1, a hollow cylindrical handpiece 2, which is supportable by one hand, has an irrigating nozzle 3 removably attached to the front end of the handpiece by a connector 31. A bore 32 extending through the connector 31 holds the irrigating nozzle 3 in communication with the interior of the handpiece 2.

An aspirating nozzle 4 is joined to the irrigating nozzle 3 and has a tip slightly projecting forward beyond the tip of the nozzle 3.

According to the embodiment, the two nozzles 3 and 4 are welded together. The rear end of the aspirating nozzle 4 is bent outward and serves as a fitting portion 41, to which an aspirating tube 42 is fitted.

The handpiece 2 is provided at its rear portion with a connecting pipe 21 and a retainer 22. A terminal pipe 23 having opposite open ends extends through and is attached to the retainer 22.

The fitting portion 41 of the aspirating nozzle 4 and the front end of the terminal pipe 23 are interconnected by the aspirating tube 42 which is flexible and made of silicone rubber. The handpiece 2 is formed on the periphery of its middle portion with a pair of lugs 24, 24 for holding the aspirating tube 42. The tube 42 extends through small holes 25 in the lugs 24.

The handpiece 2 is provided with a shutoff member 5 for opening or closing an aspirating channel 40 provided by the aspirating nozzle 4 and the aspirating tube 42.

The shutoff member 5 of the embodiment comprises a bell crank lever 50 pivoted at its bent portion to the handpiece 2, a tube pressing piece 53 provided at the free end of a short arm 52 of the lever perpendicular to the short arm 52, and a finger piece 54 extending from the free end of a long arm 51 of the lever 50. The pressing piece 53 is positioned between the lugs 24, 24 on the handpiece 2 to press the aspirating tube 42. A spring 55 disposed on the rear side of the long lever arm 51 biases the lever 50 in a direction for the pressing piece 53 to press the tube 42. The force of the spring causes the piece 53 to deform the tube 42 in pressing contact therewith to hold the aspirating channel 40 closed.

When the long arm 51 of the lever 50 is pushed against the spring 55, the pressing piece 53 releases the tube 42 from the pressure, permitting the tube to elastically restore itself and opening the aspirating channel 40.

Figure 2:
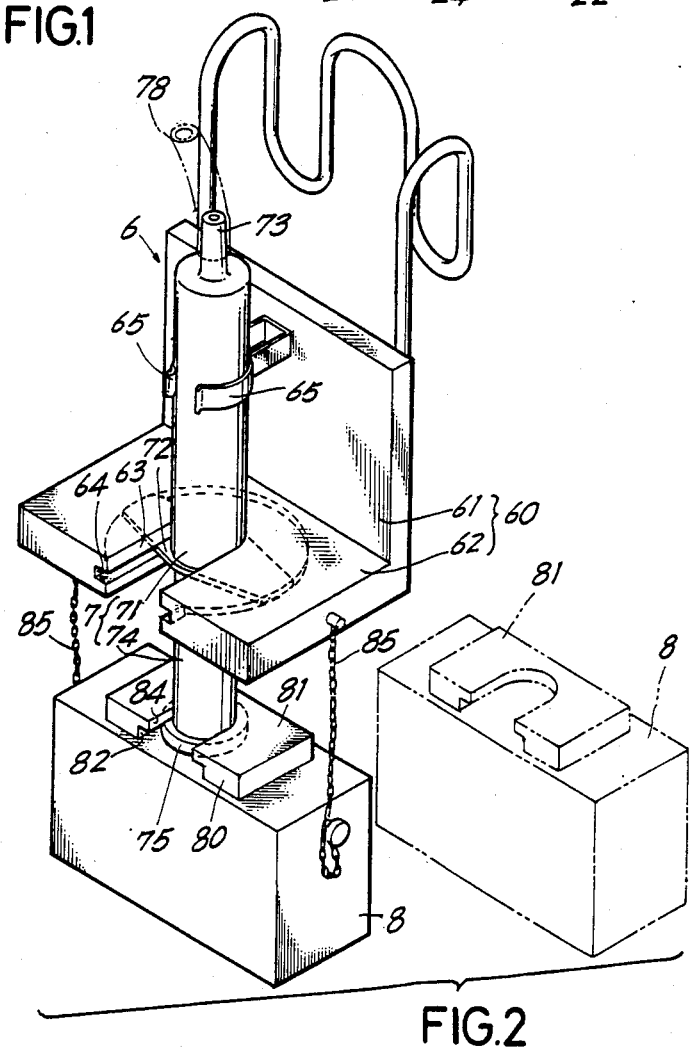
FIG. 2 is a perspective view showing a negative pressure generator of the present invention.

FIG. 2 shows a negative pressure generator 6. A mount frame 60 comprises a rectangular plate 61 having a pair of clamp spring pieces 65, 65 at an upper portion thereof, and a support block 62 at the lower end of the plate 61.

The support block 62 is centrally formed with a cutout 63 which is open at the front end of the block and extends vertically through the block. A fitting groove 64 enlarged rearward in the form of a circle is formed in the inner surface of the block defining the cutout 63.

A syringe 7 having an effective capacity of 5 to 10 c.c. is provided on the mount frame 60 with its plunger 74 extending downward. The barrel 71 of the syringe 7 has a substantially elliptical flange 72 removably fitted in the groove 64 in the mount frame 60.

Figure 3:
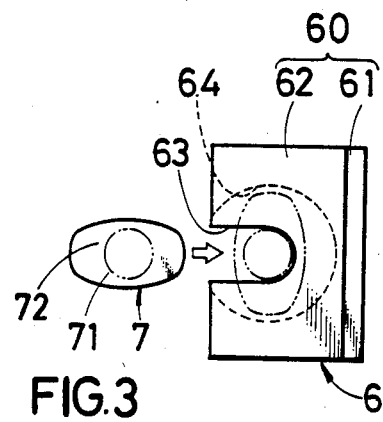
FIG. 3 is a diagram showing how to engage a barrel with a mount frame.

As seen in FIG. 3, the flange 72 can be engaged in the groove 64 by directing one end of the elliptical flange 72 toward the cutout 63 of the block 62, fitting the barrel 71 into the cutout 63 and the flange 72 into the groove 64 while placing the barrel 71 between the spring pieces 65, 65 on the plate 61, and then rotating the barrel 71 through about 90 degrees.

Because the groove 64 is constricted at the outlet of the cutout 63, the barrel 71 will not be detached from the block 62 unless the barrel 71 is rotated to the initial position. Moreover, the barrel 71 itself is clamped and supported by the spring pieces 65, 65 and is therefore prevented from slipping off the mount frame 60 inadvertently.

A tubular connector 73 extending from the upper end of the barrel 71 is connected to the terminal pipe 23 by a tube 78. The plunger 74 has a weight engaging portion 75 at its lower end.

A weight 8 is provided on its upper surface with a socket block 81 engageable with the engaging portion 75. A groove 82 is formed in a side face 80 of the socket block 81. The groove 82 is continuous with a cutout 84 formed in the upper surface of the block 81 for the plunger 74 to fit in. The weight engaging portion 75 is fitted in the groove 82 of the block 81. The weight weighs 1 to 1.5 kg.

The weight 8 and the mount frame 60 are interconnected by wires or strings 85 for preventing the plunger 74 from slipping off the barrel 71.

Figure 4:
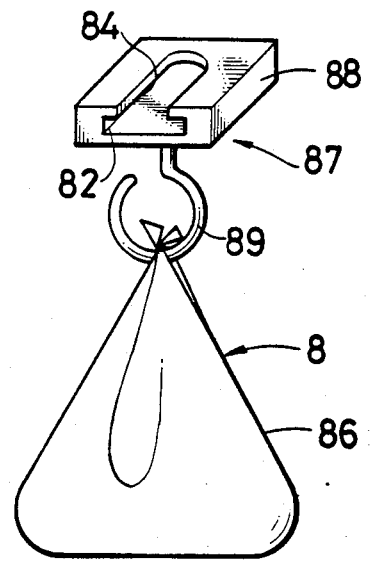
FIG. 4 is a perspective view showing another example of weight.

FIG. 4 shows another example of weight 8, which comprises a soft bag 86 made of rubber or resin and filled with water or sand. The weight 8 is attached to the engaging portion 75 of the plunger 74 by a hook member 87.

The hook member 87 comprises a plate 88 formed with a groove 82 and a plunger fittable cutout 84 like the socket block 81, and a hook 89 projecting from the lower surface of the plate 88.

Since water or sand is readily available, a heavy weight need not be carried around in this case.

Figure 5I:
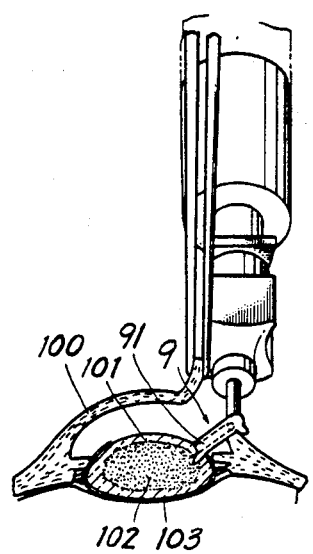
FIGS. 5(I), 5(II) and 5(III) are diagrams illustrating the procedure for surgically aspirating the lens cortex.
Figure 5:
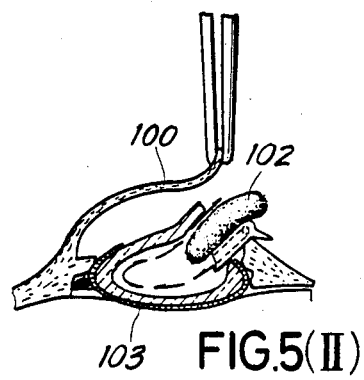

FIGS. 5(I) to 5(III) show the procedure for surgically aspirating the lens cortex with use of the present apparatus. As in the conventional method of extracapsular cataract extraction, the upper edge of the cornea 100 is first incised in a circular arc form over about ⅓ of the circumference, and the anterior lens capsule is removed. While the cornea is being pulled up, the insertion piece 91 of an irrigating cannula 9 for removing the lens nucleus is placed between the lens nucleus 102 in the lens cortex 101 and the posterior lens capsule 103 as seen in FIG. 5(I). (The illustrated irrigating cannula is proposed by the present invention in U.S. patent application Ser. No. 602,843.)

The lens nucleus 102 is slidingly forced out along the upper surface of the cannula 9 by the pressure of an irrigating solution flowing out from the cannula 9 (FIG. 5(II)).

After the lens nucleus 102 has been removed as above, the cornea is sutured. The lens cortex 101 is then to be removed. Before the removal, an instillator (not shown) containing physiological saline or like irrigating solution is connected to the connecting pipe 21 of the handpiece 2 of the aspirating apparatus of the invention by a tube 33 to connect the instillator to the irrigating nozzle 3. While the aspirating channel 40 is held closed by the shutoff member 5, the weight 8, if acting to withdraw the plunger 74, produces a negative pressure within the barrel 71, whereby withdrawal of the plunger 74 is prevented.

With the handpiece 2 held by one hand, the nozzle 3 is inserted into the eye while discharging the irrigating solution from the irrigating nozzle 3, and the lever 50 is depressed against the spring 55 to open the aspirating channel 40.

The weight 8 lowers the plunger 74, producing a negative pressure within the barrel 71 and the channel 40 and giving suction to the aspirating nozzle 4. The plunger 74 is withdrawn by the weight 8 with a constant force to maintain the suction at a constant level at all times.

The aspirating nozzle 4 is inserted into the lens cortex 101 between the sutured portions of the cornea 100 to aspirate the cortex 101 on the posterior capsule (FIG. 5(III)).

Because the irrigating solution is supplied into the lens capsule and the anterior chamber while the lens cortex 101 is being aspirated by the nozzle 4, a portion of the solution is drawn into the aspirating nozzle 4 along with the lens cortex 101, but the other portion of the solution remains between the cornea 100 and the posterior capsule 103, raising the cornea 100 away from the posterior capsule to prevent contact therebetween.

Since the negative pressure is produced by the combination of barrel, plunger and weight, there is no need to use a power supply. Moreover, the present apparatus is simple in construction, compact and convenient to carry and therefore facilitates surgery in uncivilized or secluded places.

The plunger is withdrawn by the weight, so that the force acting on the plunger remains unchanged at all times, giving a constant suction force to assure an advantageous operation.

Various changes may be made to the structure described herein without departing from the scope of the present invention which is defined by the following claims.

What is claimed is:

1. An apparatus for aspirating lens cortex comprising:
   (1) an aspirator having a handpiece, an irrigating nozzle attached to a front end of the handpiece, an aspirating nozzle adjacent to the irrigating nozzle, an aspirating tube of resilient material connected to the aspirating nozzle, and a shutoff member mounted on the handpiece for opening or closing the aspirating tube,
   (2) a negative pressure generator having a barrel attached to a mount frame and fitted therein with a plunger, said barrel having a flange, the barrel having an open connecting end for attachment of the aspirating tube, and the plunger being provided with an engaging flange portion for a weight, said barrel being provided at its outer circumference with a flange extending outwardly in the form of an ellipse, said mount frame having a support block formed at its central front end with a cutout extending rearwardly and through the support block to support said barrel, said block having a groove means between its exterior walls in the form of a circle so as to receive said barrel flange within said groove means, said plunger having a weight engaging portion at its lower end extending therefrom radially for drawing the plunger downwardly, and said weight having a socket block for fitting therein the engaging portion of the plunger and a connecting means for interconnecting the support block of the mount frame so as to prevent the plunger from slipping off.

2. The apparatus according to claim 1 wherein the weight is a bag member filled with sand or water.

* * * * *